United States Patent
Oh et al.

(10) Patent No.: US 9,602,941 B2
(45) Date of Patent: Mar. 21, 2017

(54) JACK DETECTOR AND JACK DETECTING METHOD

(71) Applicant: Fairchild Korea Semiconductor Ltd, Gyeonggi-do (KR)

(72) Inventors: Jae Young Oh, Gyeonggi-do (KR); Hyung Seok Lee, Seoul (KR)

(73) Assignee: FAIRCHILD KOREA SEMICONDUCTOR LTD. (KR)

( * ) Notice: Subject to any disclaimer, the term of this patent is extended or adjusted under 35 U.S.C. 154(b) by 421 days.

(21) Appl. No.: 14/174,394

(22) Filed: Feb. 6, 2014

(65) Prior Publication Data

US 2014/0225632 A1 Aug. 14, 2014

(30) Foreign Application Priority Data

Feb. 13, 2013 (KR) ........................ 10-2013-0015503

(51) Int. Cl.
| | |
|---|---|
| *G01R 27/08* | (2006.01) |
| *H04R 29/00* | (2006.01) |
| *H02B 1/00* | (2006.01) |
| *H04R 1/10* | (2006.01) |

(Continued)

(52) U.S. Cl.
CPC ......... *H04R 29/004* (2013.01); *G01N 27/025* (2013.01); *G01R 27/08* (2013.01); *H02B 1/00* (2013.01); *H04R 1/1041* (2013.01); *H04R 5/04* (2013.01); *H04R 2225/61* (2013.01); *H04R 2420/05* (2013.01)

(58) Field of Classification Search
CPC .... G01R 19/0092; G01R 27/14; G01R 19/00; G01R 1/203; G01R 27/08; H02B 1/00; H04R 1/1041; H04R 2225/61; G01N 27/025

USPC ......... 324/76.11–76.83, 439, 459, 522, 549, 324/600, 649, 691, 713; 381/123
See application file for complete search history.

(56) References Cited

U.S. PATENT DOCUMENTS 6,460,094 B1 * 10/2002 Hanson ............... G06F 13/4086
326/37
6,671,814 B1 * 12/2003 Kubo ................... G06F 1/3203
710/100

(Continued)

OTHER PUBLICATIONS

"U.S. Appl. No. 14/707,482, Non Final Office Action mailed Jun. 13, 2016", 17 pgs.

*Primary Examiner* — Huy Q Phan
*Assistant Examiner* — Raul Rios Russo
(74) *Attorney, Agent, or Firm* — Schwegman Lundberg & Woessner, P.A.

(57) ABSTRACT

A jack detector detects a combination state between a socket including a detecting pin and a first signal pin and a jack. The jack detector includes a first current source for supplying a first detecting current, a second current source for supplying a second detecting current larger than the first detecting current, and a buffer for generating a detecting signal in accordance with a detecting pin voltage input from the detecting pin. The second current source instead of the first current source is connected to the detecting pin in synchronization with a combination starting point when the detecting pin and the first signal pin are electrically connected to each other and it is determined that the jack is combined with the socket when the detecting signal is maintained at a state of the combination starting point.

23 Claims, 4 Drawing Sheets

(51) Int. Cl.
*G01N 27/02* (2006.01)
*H04R 5/04* (2006.01)

(56) References Cited

U.S. PATENT DOCUMENTS

| | | | | |
|---|---|---|---|---|
| 7,352,289 B1* | 4/2008 | Harris | ............... | H04Q 9/00 |
| | | | | 324/500 |
| 8,193,834 B2* | 6/2012 | Maher | ............... | H03K 5/24 |
| | | | | 327/50 |
| 2007/0245058 A1* | 10/2007 | Wurzburg | ........... | G06F 13/4022 |
| | | | | 710/313 |
| 2011/0128019 A1* | 6/2011 | Saito | ................ | H04R 5/04 |
| | | | | 324/713 |
| 2012/0239828 A1* | 9/2012 | Lin | ................ | G06F 3/162 |
| | | | | 710/16 |
| 2013/0020882 A1 | 1/2013 | Prentice | | |
| 2014/0031657 A1* | 1/2014 | McKee | ............. | A61B 5/14532 |
| | | | | 600/365 |
| 2014/0038460 A1 | 2/2014 | Lee | | |
| 2014/0043539 A1* | 2/2014 | Wang | ............... | G09G 5/006 |
| | | | | 348/723 |
| 2015/0326970 A1 | 11/2015 | Miske et al. | | |

* cited by examiner

JACK DETECTOR AND JACK DETECTING METHOD

CROSS-REFERENCE TO RELATED APPLICATION

This application claims priority to and the benefit of Korean Patent Application No. 10-2013-0015503 filed in the Korean Intellectual Property Office on Feb. 13, 2013, the entire contents of which are incorporated herein by reference.

BACKGROUND (a) Field

An exemplary embodiment relates to a device and a method for detecting whether a jack is connected with a socket. For example, whether a jack and a socket are applied to an audio device.

(b) Description of the Related Art

A detecting pin and a signal pin are formed in an audio socket with which an audio jack is combined. When the audio jack is not combined with the audio socket, it is opened between the detecting pin and the signal pin. When the audio jack is combined with the audio socket, the detecting pin and the signal pin are electrically connected so that a current may flow between the two pins.

Foreign particles may exist in the audio socket so that the detecting pin and the signal pin may be electrically conducted. That is, it may be determined that the audio jack is combined with the audio socket.

For example, moisture enters an audio socket of a smart phone so that the detecting pin and the signal pin may be electrically conducted. Then, the smart phone determines that an audio jack is combined with the audio socket to block a speaker function and to supply an audio signal to an earphone through the audio jack. However, since the audio jack is not actually connected, an erroneous operation in which an audio of the smart phone is blocked is generated.

The above information disclosed in this Background section is only for enhancement of understanding of the background of the invention and therefore it may contain information that does not form the prior art that is already known in this country to a person of ordinary skill in the art.

SUMMARY

An exemplary embodiment has been made in an effort to provide an audio jack detector and an audio jack detecting method having advantages of correctly detecting whether an audio jack is combined with an audio socket. An exemplary embodiment provides an audio jack detector and an audio jack detecting method capable of correctly detecting whether an audio jack is combined with an audio socket.

According to an exemplary embodiment, a jack detector for detecting a combination state between a socket including a detecting pin and a first signal pin and a jack includes a first current source configured to supply a first detecting current, a second current source configured to supply a second detecting current larger than the first detecting current, and a buffer configured to generate a detecting signal in accordance with a detecting pin voltage input from the detecting pin. After the second current source instead of the first current source is connected to the detecting pin in synchronization with a combination starting point when the detecting pin and the first signal pin are electrically connected to each other, it is determined that the jack is combined with the socket when the detecting signal is maintained at a state of the combination starting point.

The jacket detector further includes a first switch connected between the first current source and the detecting pin, a second switch connected between the second current source and the detecting pin. The first switch is turned on and the second switch is turned off until at least the combination starting point. The first switch is turned off and the second switch is turned on after a predetermined delay from the combination starting point.

The buffer generates a first level detecting signal when the detecting pin voltage is larger than a predetermined reference voltage and generates a second level detecting signal when the detecting voltage is smaller than the reference voltage.

The jack detector further includes a controller configured to sense the combination starting point using the detecting signal and control a connection between the first current source and the detecting pin and a connection between the second current source and the detecting pin in synchronization with the combination starting point.

The controller senses a point in time when the detecting signal is changed from a first level to a second level as the combination starting point and generates an enable signal when the detecting signal is maintained at the second level after the combination starting point.

The jack detector further includes a first switch connected between the first current source and the detecting pin and a second switch connected between the second current source and the detecting pin.

The controller generates a first switch signal at a level where the first switch is turned on and a second switch signal at a level where the second switch is turned off until at least the combination starting point and generates the first switch signal at a level where the first switch is turned off and the second switch signal at a level where the second switch is turned on after a predetermined delay from the combination starting point.

A signal is supplied to the first receiving pin in accordance with the enable signal.

The jack includes a terminal connected to the detecting pin and the first receiving pin when the jack is combined with the socket.

According to an exemplary embodiment, a method of detecting a combination state between a socket including a detecting pin and a first signal pin and a jack includes supplying a first detecting current to the detecting pin, generating a detecting signal in accordance with a detecting pin voltage input from the detecting pin, supplying a second detecting current larger than the first detecting current to the detecting pin instead of the first detecting current in synchronization with a combination starting point when the detecting pin and the first signal pin are electrically connect to each other, and determining that the jack is combined with the socket when the detecting signal is maintained at a state of the combination starting point at a point in time when the detecting signal is detected after the second detecting current is supplied to the detecting pin.

Generating the detecting signal includes generating a first level detecting signal when the detecting pin voltage is larger than a predetermined reference voltage and generating a second level detecting signal when the detecting voltage is smaller than the reference voltage.

The jack detecting method further includes sensing a point in time when the detecting signal is changed from a first level to a second level as the combination starting point.

The jack detecting method further includes generating the enable signal when it is determined that the jack is combined with the socket.

The jack detecting method further includes supplying a signal to the first receiving pin in accordance with the enable signal. The jack includes a terminal connected to the detecting pin and the first receiving pin when the jack is combined with the socket.

According to an exemplary embodiment, a jack detector for detecting a combination state between a socket including a detecting pin and a first signal pin and a jack includes a variable current source configured to supply a current to the detecting pin and a buffer configured to generate a detecting signal in accordance with a detecting pin voltage input from the detecting pin. A current of the variable current source is changed in synchronization with a combination starting point when the detecting pin and the first signal pin are electrically connected to each other and, after the current of the variable current source is changed, when the detecting signal is maintained at a state of the combination starting point, it is determined that the jack is combined with the socket.

A detecting current of the variable current source is increased in synchronization with the combination starting point.

The buffer generates a first level detecting signal when the detecting pin voltage is larger than a predetermined reference voltage and generates a second level detecting signal when the detecting voltage is smaller than the reference voltage.

The jack detector further include a controller configured to sense the combination starting point using the detecting signal and control the variable current source so that the detecting current is increased in synchronization with the combination starting point.

The controller senses a point in time when the detecting signal is changed from a first level to a second level as the combination starting point and generates an enable signal when the detecting signal is maintained at the second level after the combination starting point.

According to the exemplary embodiment of the invention, a jack detector and a jack detecting method capable of correctly detecting whether the jack is combined with the socket is provided.

DETAILED DESCRIPTION OF THE EMBODIMENTS

In the following detailed description, only certain exemplary embodiments have been shown and described, simply by way of illustration. As those skilled in the art would realize, the described embodiments may be modified in various different ways, all without departing from the spirit or scope of the invention. Accordingly, the drawings and description are to be regarded as illustrative in nature and not restrictive. Like reference numerals designate like elements throughout the specification.

Throughout this specification and the claims that follow, when it is described that an element is "coupled" to another element, the element may be "directly coupled" to the other element or "electrically coupled" to the other element through a third element. In addition, unless explicitly described to the contrary, the word "comprise" and variations such as "comprises" or "comprising" will be understood to imply the inclusion of stated elements but not the exclusion of any other elements.

Hereinafter, a jack detector and a jack detecting method according to an exemplary embodiment will be described with reference to the drawings. To explain the exemplary embodiment, a jack and a socket are applied to the audio device, for example, an audio jack and an audio socket. However, the invention is not limited thereto.

Figure 1:
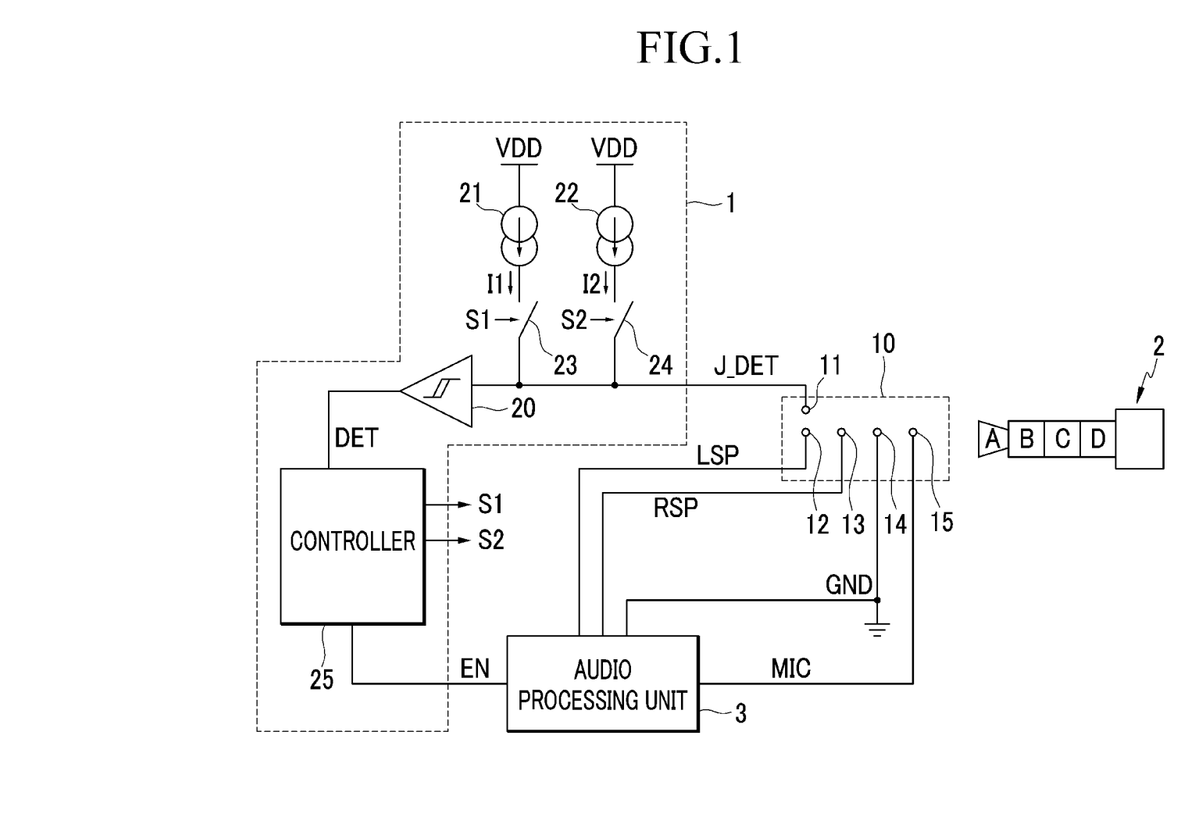
FIG. 1 is a view illustrating a structure of an audio jack detector according to an exemplary embodiment.

FIG. 1 is a view illustrating a structure of an audio jack detector according to an exemplary embodiment. In FIG. 1, in order to describe an audio jack detector 1, an audio socket 10, an audio jack 2, and an audio processing unit 3 are illustrated together.

An audio device including the audio jack detector 1, the audio socket 10, and the audio processing unit 3 may be applied to various devices. For example, the audio device may be applied to a mobile phone, a tablet PC, and a laptop.

The audio socket 10 includes a detecting pin 11, a first signal pin 12, a second signal pin 13, a ground pin 14, and a mike pin 15. In FIG. 1, the audio jack detector 1 and the audio socket 10 are separated from each other. However, the exemplary embodiment is not limited thereto. The audio socket 10 may be combined with the audio jack detector 1 according to the exemplary embodiment to realize a device.

The audio processing unit 3 receives an enable signal EN from the audio jack detector 1 and determines whether the audio jack 2 is combined with the audio socket 10 in accordance with the enable signal EN. The audio processing unit 3 determines whether the audio jack 2 is combined with the audio socket 10 and may supply a left audio signal LSP and a right audio signal RSP to the first signal pin 12 and the second signal pin 13, respectively.

Furthermore, the audio processing unit 3 may supply a bias current to the mike pin 15 and may signal process an input of the mike pin 15 when the input MIC is sensed by the mike pin 15 to generate an audio signal.

The audio processing unit 3 is connected to a ground GND and an output signal generated by the audio processing unit 3 is based on the ground GND.

The audio jack 2 includes a left audio terminal A, a right audio terminal B, a ground terminal C, and a mike terminal D. When the audio jack 2 is combined with the audio socket 10, the left audio terminal A is connected to the detecting pin 11 and the first signal pin 12, the right audio terminal B is connected to the second signal pin 13, the ground terminal C is connected to the ground pin 14, and the mike terminal D is connected to the mike pin 15.

The audio jack detector 1 includes a buffer 20, a first current source 21, a second current source 22, a first switch 23, a second switch 24, and a controller 25.

The first current source 21 generates a first detecting current I1. The second current source 22 generates a second detecting current I2. The first switch 23 is connected between the first current source 21 and the detecting pin 11 and the second switch 24 is connected between the second current source 22 and the detecting pin 11.

The first switch 23 performs a switching operation in accordance with a first switch signal S1 supplied from the controller 25. For example, the first switch 23 is turned on when the first switch signal S1 is at a high level and is turned off when the first switch signal S1 is at a low level.

The buffer 20 generates a detecting signal DET in accordance with states of the detecting pin 11 and the first signal pin 12. To be specific, a detecting pin voltage J_DET that is a voltage of the detecting pin 11 is determined in accordance with resistance between the detecting pin 11 and the first signal pin 12 and the buffer 20 outputs the detecting signal DET in accordance with the detecting pin voltage J_DET.

The buffer 20 may have a hysterisis characteristic. Then, it is possible to prevent a level of the detecting signal DET from being changed by noise of the detecting pin voltage J_DET. The buffer 20 may output a predetermined high level when the detecting pin voltage J_DET is larger than a predetermined reference voltage and may output a predetermined low level when the detecting pin voltage J_DET is smaller than the predetermined reference voltage.

When the detecting pin 11 and the first signal pin 12 are not connected to each other, it is opened between the detecting pin 11 and the first signal pin 12. Then, the detecting pin voltage J_DET is maintained at a high level by the first detecting current I1 of the first current source 21 and the buffer 20 receives the high level detecting pin voltage J_DET to output a high level detecting signal DET.

When the detecting pin 11 and the first signal pin 12 are electrically connected to each other, the first detecting current I1 of the first current source 21 or the second detecting current I2 of the second current source 22 flows between the detecting pin 11 and the first signal pin 12, the detecting pin voltage J_DET determined in accordance with the resistance between the detecting pin 11 and the first signal pin 12 is input to the buffer 20, and the buffer 20 outputs the detecting signal DET determined in accordance with the input detecting pin voltage J_DET.

To be specific, when the audio jack 2 is combined with the audio socket 10, the resistance between the detecting pin 11 and the first signal pin 12 is low. Therefore, the detecting pin voltage J_DET input to the buffer 20 is at a low level and the buffer 20 outputs a low level detecting signal DET.

According to the exemplary embodiment, the second detecting current I2 is remarkably larger than the first detecting current I1. For example, when the first detecting current I1 is 0.5 µA, the second detecting current I2 may be 300 µA.

In a state where the audio jack 2 is combined with the audio socket 10, although the second detecting current I2 instead of or together with the first detecting current I1 flows between the detecting pin 11 and the first signal pin 12, the detecting pin voltage J_DET input to the buffer 20 is at a low level. That is, in a state where the audio jack 2 is combined with the audio socket 10, the difference between the detecting signal DET at a combination starting point (i.e., at this instance, the first detecting current I1 flows between the detecting pin 11 and the first signal pin 12) and the detecting signal DET after the second detecting current I2, instead of or together with the first detecting current I1, flows between the detecting pin 11 and the first signal pin 12, is smaller than a predetermined level. For example, the buffer 20 maintains the low level detecting signal DET after the second detecting current I2, instead of or together with the first detecting current I1, flows between the detecting pin 11 and the first signal pin 12, in the same manner as the detecting signal DET at the combination starting point.

However, when not the audio jack 2 but foreign particles (e.g., moisture) exist between the detecting pin 11 and the first signal pin 12, the resistance between the two pins 11 and 12 is very large. When the second detecting current I2 flows between the detecting pin 11 and the first signal pin 12, the detecting pin voltage J_DET is at a high level and the buffer 20 outputs a high level detecting signal DET in accordance with the high level detecting pin voltage J_DET. An input voltage is at a high level.

The controller 25 detects whether the audio jack 2 is combined with the audio socket 10 using the detecting signal DET. The second current source 22 instead of the first current source 21 is connected to the detecting pin 11 in synchronization with a combination starting point.

The combination starting point means a point in time when the detecting pin 11 is electrically separated from the first signal pin 12 and is then connected to the first signal pin 12. At the combination starting point, the audio jack 2 or the foreign particles may be connected between the detecting pin 11 and the first signal pin 12.

The controller 25 determines that the audio jack 2 is combined with the audio socket 10 when a level of the detecting signal DET is maintained at a level of the combination starting point after the second current source 22 is connected to the detecting pin 11. The controller 25 generates the enable signal EN when it is determined that the audio jack 2 is combined with the audio socket 10.

To be specific, the controller 25 generates the high level first switch signal S1 for turning on the first switch 23 and generates the low level second switch signal S2 for turning off the second switch 24 when the detecting signal DET is at a high level.

The controller 25 generates the low level first switch signal S1 for turning off the first switch 23 and generates the high level second switch signal S2 for turning on the second switch 24 after a predetermined delay from the combination starting point when the detecting signal DET is reduced to a low level. Then, the second detecting current I2 instead of the first detecting current I1 is supplied to the detecting pin 11.

The controller 25 generates the enable signal EN when it is determined that the low level detecting signal DET is maintained after the second detecting current I2 starts to be supplied.

As described above, when the foreign particles exist between the detecting pin 11 and the first signal pin 12, the detecting pin voltage J_DET is increased by the second detecting current I2 so that a level the detecting signal DET is also increased. When the level of the detecting signal DET is reduced and then, is increased within a predetermined period, the controller 25 determines that not the audio jack 2 but the foreign particles exist between the detecting pin 11 and the first signal pin 12 not to generate the enable signal EN.

Figure 2:
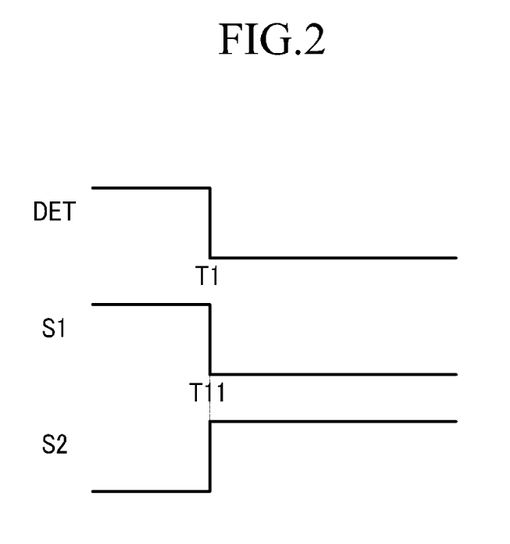
FIG. 2 is a waveform diagram illustrating changes in a detecting signal, a first switch signal, and a second switch signal when an audio jack is combined with an audio socket.

FIG. 2 is a waveform diagram illustrating changes in a detecting signal, a first switch signal, and a second switch signal when an audio jack is combined with an audio socket.

Figure 3:
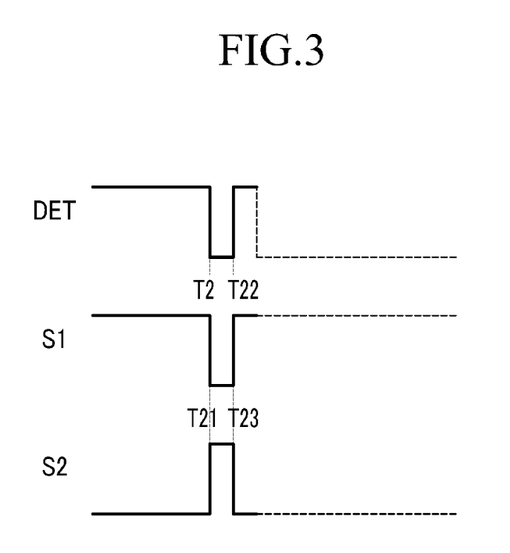
FIG. 3 is a waveform diagram illustrating changes in a detecting signal, a first switch signal, and a second switch signal when foreign particles exist in an audio socket.

FIG. 3 is a waveform diagram illustrating changes in a detecting signal, a first switch signal, and a second switch signal when foreign particles exist in an audio socket.

As illustrated in FIG. 2, when the detecting signal DET is reduced to a low level at a point in time T1, the controller 25 reduces the first switch signal S1 to a low level and increases the second switch signal S2 to a high level at a point in time T11 in synchronization with a falling edge of the detecting signal DET. For example, there is a delay from the point in time T1 to the point in time T11. Then, the second detecting current I2 is flown to the detecting pin 11.

Since the audio jack 2 is combined with the audio socket 10, although the detecting pin voltage J_DET is increased by the second detecting current I2, the detecting pin voltage J_DET belongs to a low level range. Therefore, the detecting signal DET is maintained at a low level. Since the detecting signal DET is maintained at the low level after the second detecting current I2 is supplied, the controller 25 generates the enable signal EN.

For example, under a condition where the detecting signal DET is generated by the second detecting current I2, when the controller 25 detects the detecting signal DET, the detecting signal DET is sensed at a low level.

As illustrated in FIG. 3, when the detecting signal DET is reduced to a low level at a point in time T2, the controller 25 reduces the first switch signal S1 to a low level and increases the second switch signal S2 to a high level at a point in time T21 in synchronization with the falling edge of the detecting signal DET. For example, there is a delay from the point in time T2 to the point in time T21. Then, the second detecting current I2 is flown to the detecting pin 11.

Since not the audio jack 2 but the foreign particles are combined with the audio socket 10, the detecting pin voltage J_DET is increased to a high level by the second detecting current I2 and the detecting signal DET is increased to a high level at a point in time T22.

Since the detecting signal DET is increased from a low level to a high level after the second detecting current I2 is supplied, the controller 25 does not generate the enable signal EN.

Furthermore, the controller 25 increases the first switch signal S1 to a high level and reduces the second switch signal S2 to a low level at a point in time T23. Then, the first detecting current I1 is supplied to the detecting pin 11. In a state where the foreign particles are not removed, as illustrated by a dotted line, the detecting signal DET may be reduced to a low level again.

As illustrated in a waveform marked with a dotted line after the point in time T22 in FIG. 3, the controller 25 may not change levels of the first switch signal S1 and the second switch signal S2 in a predetermined protecting period although the detecting signal DET is reduced to the low level again.

In FIG. 1, it is illustrated that the audio jack detector includes the two current sources 21 and 22. However, the exemplary embodiment is not limited thereto. For example, instead of the two current sources 21 and 22, a variable current source may be included.

Figure 4:
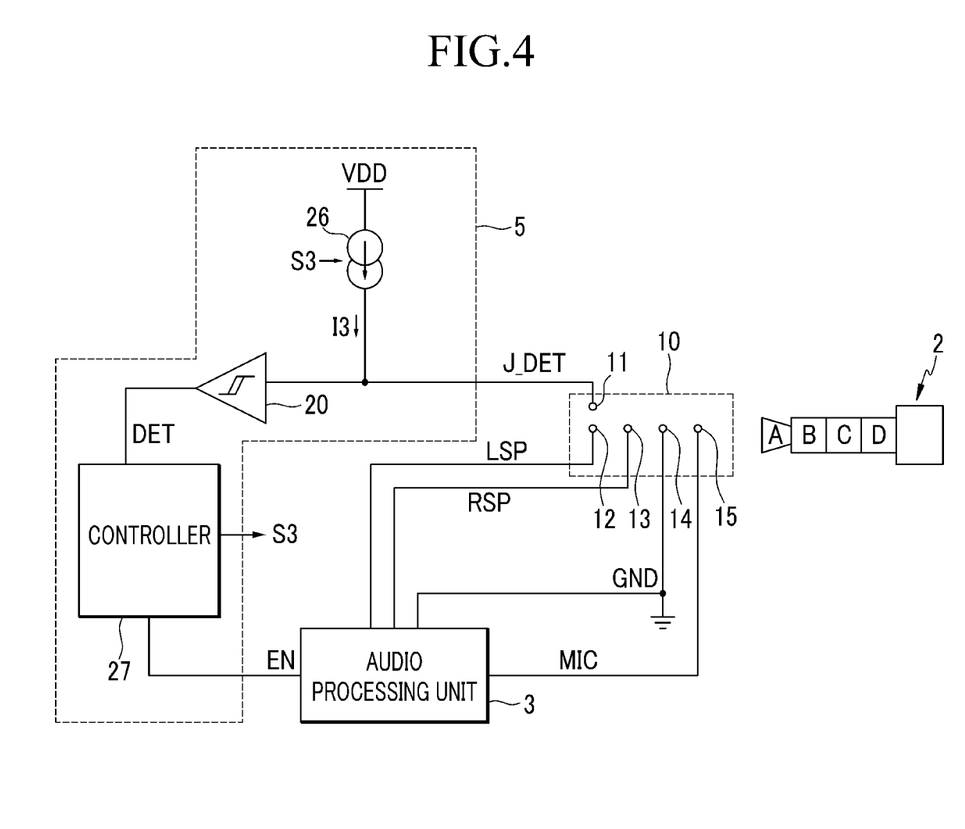
FIG. 4 is a view illustrating an audio jack detector according to another exemplary embodiment.

FIG. 4 is a view illustrating an audio jack detector according to another exemplary embodiment.

In FIG. 4, in order to describe an audio jack detector 5, an audio socket 10, an audio jack 2, and an audio processing unit 3 are illustrated together. In FIG. 4, the same elements as those of the above-described exemplary embodiment are denoted by the same reference numerals. Furthermore, the current exemplary embodiment is compared with the above-described exemplary embodiment and description of the same elements will be omitted.

A variable current source 26 changes a third detecting current I3 in accordance with a variable signal S3 output from a controller 27. The variable current source 26 is connected to the detecting pin 11.

The detecting pin voltage J_DET determined in accordance with the resistance between the detecting pin 11 and the first signal pin 12 is input to the buffer 20. The buffer 20 generates the detecting signal DET in accordance with the detecting pin voltage J_DET by the above-described method.

The controller 27 senses whether the audio jack 2 is combined with the audio socket 10 using the detecting signal DET. The controller 25 controls the variable current source 26 so that a current of the variable current source 26 is increased in synchronization with the combination starting point.

For example, the controller 27 determines that the audio jack 2 is combined with the audio socket 10 when a level of the detecting signal DET is maintained at a level of the combination starting point after the third detecting current I3 of the variable current source 26 is increased. When it is determined that the audio jack 2 is combined with the audio socket 10, the controller 27 may generate the enable signal EN.

When a level of the detecting signal DET is increased within a predetermined period after the third detecting current I3 of the variable current source 26 is increased, the controller 27 determines that not the audio jack 2 but the foreign particles exist between the detecting pin 11 and the first signal pin 12. Then, the controller 27 may not generate the enable signal EN.

The controller 27 generates a control signal S3 for controlling a current generating operation of the variable current source 26. For example, the variable current source 26 may generate a current of the same magnitude as that of the first detecting current I1 when the control signal S3 is at a low level and may generate a current of the same magnitude as that of the second detecting current I2 when the control signal S3 is at a high level.

Figure 5:
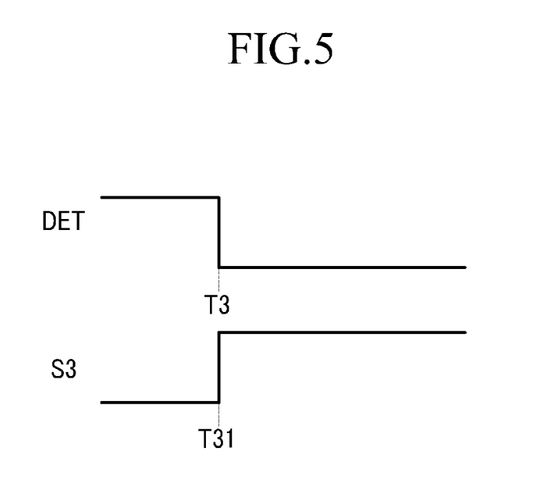
FIG. 5 is a waveform diagram illustrating changes in a detecting signal and a control signal when an audio jack is combined with an audio socket.

FIG. 5 is a waveform diagram illustrating changes in a detecting signal and a control signal when an audio jack is combined with an audio socket.

Figure 6:
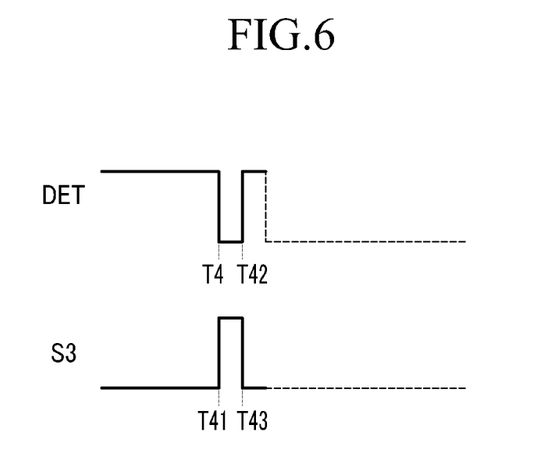
FIG. 6 is a waveform diagram illustrating changes in a detecting signal and a control signal when foreign particles exist in an audio socket.

FIG. 6 is a waveform diagram illustrating changes in a detecting signal and a control signal when foreign particles exist in an audio socket.

As illustrated in FIG. 5, when the detecting signal DET is reduced to a low level at a point in time T3, the controller 27 increases the control signal S3 to a high level in synchronization with a falling edge of the detecting signal DET. For example, there is a delay from the point in time T3 to the point in time T31. Then, the variable current source 26 increases the detecting current I3.

Since the audio jack 2 is combined with the audio socket 10, although the detecting pin voltage J_DET is increased by the second detecting current I2, the detecting pin voltage J_DET belongs to a low level range. Therefore, the detecting signal DET is maintained at a low level. Since the detecting signal DET is maintained at a low level after the detecting current I3 is increased, the controller 27 generates the enable signal EN.

For example, under a condition where the detecting signal DET is generated by the increased detecting current I3, when the controller 27 detects the detecting signal DET, the detecting signal DET is sensed at a low level.

As illustrated in FIG. 6, when the detecting signal DET is reduced to a low level at a point in time T4, the controller 27 increases the control signal S3 to a high level at a point in time T41 in synchronization with the falling edge of the detecting signal DET. For example, there is a delay from the point in time T4 to the point in time T41. Then, the variable current source 26 increases the detecting current I3.

Since not the audio jack 2 but the foreign particles are combined with the audio socket 10, the detecting pin voltage J_DET is increased to a high level by the increased detecting current I3 and the detecting signal DET is increased to a high level at a point in time T42.

Since the detecting signal DET is increased from a low level to a high level after the detecting current I3 is increased, the controller 27 does not generate the enable signal EN.

Furthermore, the controller 27 reduces the control signal S3 to a low level at a point in time T43. Then, the detecting current I3 that is not increased is supplied to the detecting pin 11. In a state where the foreign particles are not removed, as marked with a dotted line, the detecting signal DET may be reduced to a low level again.

As illustrated in a waveform marked with a dotted line after a point in time T42 in FIG. 6, the controller 25 may not change a level of the control signal S3 in a predetermined protecting period although the detecting signal DET is reduced to a low level again.

In another example, the controller 25 may maintain a high level of the control signal S3 after the point in time T43 or change the level of the control signal S3 to a high level or a low level in turn after the point in time T43.

As described above, the audio jack detector according to the exemplary embodiment changes a detecting current when an electrical connection between the detecting pin and the first signal pin is sensed to determine whether the connection is performed by the foreign particles or the audio jack. It is possible to more correctly detect whether the audio jack is connected to the audio socket than in a conventional art.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

DESCRIPTION OF SYMBOLS audio jack detectors 1, 5
audio jack 2
audio processing unit 3
audio socket 10
buffer 20
first current source 21
second current source 22,
variable current source 26
first switch 23
second switch 24
controllers 25, 27
left audio terminal A
right audio terminal B
ground terminal C
mike terminal D
detecting pin 11
first signal pin 12
second signal pin 13
ground pin 14
mike pin 15

What is claimed is:

1. A jack detector for detecting a combination state between a jack and an audio socket, the audio socket including a detecting pin and a first signal pin, the jack detector comprising:
   a first current source and configured to selectively supply a first detecting current to the detecting pin;
   a second current source configured to selectively supply a second detecting current larger than the first detecting current to the detecting pin; and
   a buffer coupled to the detecting pin and configured to generate a detecting signal in accordance with a detecting pin voltage input from the detecting pin,
   the jack detector operable to determine that the jack is combined with the audio socket when a difference between the detecting signal at a combination starting point when the detecting pin and the first signal pin are electrically connected to each other and the first detecting current is supplied to the detecting pin, and the detecting signal after the second detecting current is supplied to the detecting pin in synchronization with the combination starting point, is smaller than a predetermined reference voltage.

2. The jack detector of claim 1, further comprising:
   a first switch connected between the first current source and the detecting pin;
   a second switch connected between the second current source and the detecting pin;
   wherein the first switch is operable to be turned on and the second switch is operable to be turned off at least until the combination starting point is detected; and
   wherein the first switch is operable to be turned off and the second switch is operable to be turned on after a predetermined delay from the combination starting point.

3. The jack detector of claim 1, wherein the buffer is operable to generate a first level detecting signal when the detecting pin voltage is larger than the predetermined reference voltage and is operable to generate a second level detecting signal when the detecting voltage is smaller than the reference voltage.

4. The jack detector of claim 1, further comprising
   a controller configured to sense the combination starting point using the detecting signal and to control a connection between the first current source and the detecting pin and a connection between the second current source and the detecting pin in synchronization with the combination starting point.

5. The jack detector of claim 4, wherein the controller senses a point in time when the detecting signal is changed from a first level to a second level as the combination starting point and generates an enable signal when the detecting signal is maintained at the second level after the combination starting point.

6. The jack detector of claim 5, further comprising:
   a first switch connected between the first current source and the detecting pin; and
   a second switch connected between the second current source and the detecting pin.

7. The jack detector of claim 6, wherein the controller generates a first switch signal at a level where the first switch is turned on and a second switch signal at a level where the second switch is turned off until at least the combination starting point and generates the first switch signal at a level where the first switch is turned off and the second switch signal at a level where the second switch is turned on after a predetermined delay from the combination starting point.

8. The jack detector of claim 5, wherein a signal is supplied to the first receiving pin in accordance with the enable signal.

9. The jack detector of claim 1, wherein the jack comprises a terminal connected to the detecting pin and the first receiving pin when the jack is combined with the audio socket.

10. A method of detecting a combination state between an audio socket including a detecting pin and a first signal pin and a jack, the method comprising:
- supplying a first detecting current to the detecting pin;
- generating a detecting signal in accordance with a detecting pin voltage input from the detecting pin;
- supplying a second detecting current larger than the first detecting current to the detecting pin instead of the first detecting current in synchronization with a combination starting point when the detecting pin and the first signal pin are electrically connect to each other; and
- determining that the jack is combined with the audio socket when the detecting signal is maintained at a state of the combination starting point at a point in time when the detecting signal is detected after the second detecting current is supplied to the detecting pin.

11. The method of claim 10, wherein:
generating the detecting signal comprises:
- generating a first level detecting signal when the detecting pin voltage is larger than a predetermined reference voltage; and
- generating a second level detecting signal when the detecting voltage is smaller than the reference voltage.

12. The method of claim 11, further comprising:
sensing a point in time when the detecting signal is changed from a first level to a second level as the combination starting point.

13. The method of claim 10, further comprising:
generating the enable signal when it is determined that the jack is combined with the audio socket.

14. The method of claim 13, further comprising:
supplying a signal to the first receiving pin in accordance with the enable signal.

15. The method of claim 10, wherein the jack comprises a terminal connected to the detecting pin and the first receiving pin when the jack is combined with the audio socket.

16. A detection device comprising:
- a detection circuit configured to selectively apply a first current to a detecting pin of an audio socket and to selectively apply a second current to the detecting pin of an audio socket according to a voltage of the detecting pin generated from the first current; and
- a level circuit configured to generate levels that correspond to voltages of the detecting pin generated from the first current and the second current,
- wherein it is determined whether a detection object is a jack or not according to a result of a comparison between the level generated at the detecting pin from to the first current and the level generated at the detecting pin from the second current.

17. The detection device of claim 16, wherein the detection circuit comprises:
- a first current source configured to supply the first current,
- a second current source configured to supply the second current,
- a first switch connected between the first current source and the terminal, and
- a second switch connected between the second current source and the terminal, and
- the first switch is controlled to be turned on and the second switch is controlled to be turned off until before the detection object touches a terminal coupled to the detecting pin and the first switch is controlled to be turned off and the second switch is controlled to be turned on after the detection object touches the terminal.

18. The detection device of claim 16, wherein the level circuit is configured to generate a first level when the voltage of the detecting pin is higher than a reference voltage and to generate a second level when the voltage of the detecting pin is lower than the reference voltage.

19. The detection device of claim 18, wherein, when an output of the level circuit is maintained with the second level after the output is changed to the second level from the first level, the detection object is determined to be a jack.

20. The detection device of claim 16, wherein the detection circuit comprises a variable current source configured to generate the first current until before the detection object touches the terminal and generating the second current after the detection object touches the terminal.

21. The detection device of claim 20, wherein, when an output of the level circuit is maintained at a state of an instant of change of the variable current source after current change of the variable current source occurs, the detection object is determined to be the jack.

22. The detection device of claim 17, wherein the terminal comprises a first signal pin and a detection pin that are electrically connected with each other through the jack.

23. The detection device of claim 17, wherein the jack is an audio jack and the terminal is in an audio socket that corresponds to the audio jack.

* * * * *